United States Patent [19]

Masateru et al.

[11] Patent Number: 4,644,071

[45] Date of Patent: Feb. 17, 1987

[54] ARALKOXY AND ARYLOXYALKOXY KOJIC ACID DERIVATIVES

[75] Inventors: Miyano Masateru, Northbrook; Robert L. Shone, Palatine, both of Ill.

[73] Assignee: G. D. Searle & Co., Skokie, Ill.

[21] Appl. No.: 629,916

[22] Filed: Jul. 11, 1984

[51] Int. Cl.$^4$ ........................................... C07D 315/00
[52] U.S. Cl. ..................................................... 549/417
[58] Field of Search ................................. 549/418, 417

[56] References Cited

U.S. PATENT DOCUMENTS

| | | | |
|---|---|---|---|
| 2,865,930 | 12/1958 | Metivier et al. | 549/417 |
| 3,953,604 | 4/1976 | Warren | 424/283 |
| 4,006,245 | 2/1977 | Augstein et al. | 424/283 |
| 4,213,903 | 7/1980 | Bantick et al. | 548/250 |
| 4,238,495 | 12/1980 | Warren et al. | 424/269 |
| 4,304,728 | 12/1981 | Clark et al. | 549/418 |

FOREIGN PATENT DOCUMENTS 1291864 12/1969 United Kingdom .

OTHER PUBLICATIONS

M. Griffin et al., "Effects of Leukotriene D on the Airways in Asthma", *N. Engl. J. Med.*, 308, 436-439 (1983).

R. A. Lewis & K. F. Austen, "Mediation of Local Homeostasis and Inflammation by Leukotrienes and Other Mast Cell-Dependent Compounds", *Nature*, 293, 103-108 (1981).

F. Michelassi et al., "Leukotriene D$_4$: A Potent Coronary Artery Vasoconstrictor Associated with Impaired Ventricular Contraction," *Science*, 217, 841-843 (1982).

J. A. Burke et al., "Leukotrienes C$_4$, D$_4$ and E$_4$: Effects on Human and Guinea-Pig Cardiac Preparations in Vitro," *J. Pharmacol. and Exp. Therap.*, 221, 235-241 (1982).

R. A. Appleton et al., "Antagonists of Slow Reacting Substance of Anaphylaxis, Synthesis of a Series of Chromone-2-Carboxylic Acids", *J. Med. Chem.*, 20, 371-379 (1977).

*Primary Examiner*—Ethel G. Love
*Attorney, Agent, or Firm*—John J. McDonnell; R. E. L. Henderson

[57] ABSTRACT

This invention relates to substituted aralkoxy and aryloxyalkoxy kojic acid derivatives, which are useful as leukotriene D$_4$(LTD$_4$) inhibitors and therefore useful in the treatment of allergies, inflammatory conditions, and coronary vasoconstriction.

20 Claims, No Drawings

ARALKOXY AND ARYLOXYALKOXY KOJIC ACID DERIVATIVES

BACKGROUND OF THE INVENTION (a) Field of the Invention

This invention in its broadest aspect relates to inhibitors of metabolic pathways. In particular, the invention relates to novel compounds of Formula I, which are inhibitors of leukotriene $D_4$ ($LTD_4$) and which therefore are useful to prevent or alleviate the symptoms associated with $LTD_4$, such as allergic reactions, particularly asthma, see M. Griffin et al., *N. Engl. J. Med.*, 308, 436 (1983); inflammatory conditions; and coronary vasoconstriction.

$LTD_4$ is a product of the 5-lipoxygenase pathway and is the major active constituent of slow reacting substance of anaphylaxis (SRS-A), a potent bronchoconstrictor that is released during allergic reactions. See R. A. Lewis and K. F. Austen, *Nature*, 293, 103–108 (1981). When administered to humans and guinea pigs, $LTD_4$ causes bronchoconstriction by two mechanisms: (1) directly by stimulating smooth muscle; and (2) indirectly through release of thromboxin $A_2$, which causes contraction of respiratory smooth muscle. Because antihistamines are ineffective in the management of asthma, SRS-A is believed to be a mediator of the bronchoconstriction occurring during an allergic attack. $LTD_4$ may also be involved in other inflammatory conditions such as rheumatoid arthritis. Furthermore, $LTD_4$ is a potent coronary vasoconstrictor and influences contractile force in the myocardium and coronary flow rate of the isolated heart. See F. Michelassi et al., *Science*, 217, 841 (1982); J. A. Burke et al., *J. Pharmacol. and Exp. Therap.*, 221, 235 (982).

(b) Prior Art

A number of aryloxyalkoxy benzopyrans and benzopyranones have been disclosed as useful leukotriene inhibitors. See., e.g., U.S. Pat. Nos. 4,238,495, 4,213,903, 4,006,245, and 3,953,604; British Pat. No. 1,291,864; and R. A. Appleton et al., *J. Med. Chem.*, 20, 371–379 (1977). The compounds of this invention represent the first class of $LTD_4$ inhibitors in which a pyranone moiety is not ring-fused to a benzene ring and is instead attached directly to an aryloxyalkoxy or aralkoxy substituent.

SUMMARY OF THE INVENTION

The invention relates to compounds of Formula I:

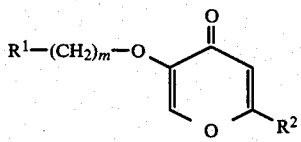

wherein $R^1$ is:

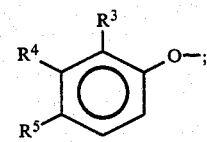

(a)

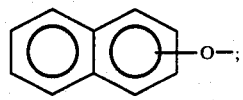

(b)

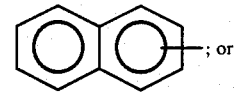

(c)

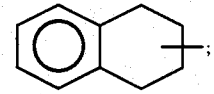

(d)

wherein $R^2$ is:
(a) $CH_2OH$;
(b) $CH=O$; or
(c) $COOR^6$;

Wherein $R^3$ is:
(a) hydrogen;
(b) alkyl of 1 to 6 carbon atoms, inclusive; or
(c) alkenyl of 2 to 6 carbon atoms, inclusive;

wherein $R^4$ is:
(a) hydrogen; or
(b) hydroxy;

wherein $R^5$ is:
(a) hydrogen; or
(b) alkanoyl of 2 to 6 carbon atoms, inclusive;

wherein $R^6$ is:
(a) hydrogen;
(b) alkyl of 1 to 6 carbon atoms, inclusive;
(c) alkali metal ion; or
(d) $R^7R^8R^9R^{10}N^+$;

wherein $R^7$, $R^8$, $R^9$, and $R^{10}$, each being the same or different, are:
(a) hydrogen; or
(b) alkyl of 1 to 6 carbon atoms, inclusive; wherein m is an integer from 1 to 10, inclusive.

Examples of alkyl of 1 to 6 carbon atoms, inclusive, are methyl, ethyl, propyl, butyl, pentyl, hexyl, and the isomeric forms thereof, generally referred to as alkyl.

Examples of alkenyl of 2 to 6 carbon atoms, inclusive, are ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, and the isomeric forms thereof.

Examples of alkanoyl of 2 to 6 carbon atoms, inclusive, are acetyl, propanoyl, butanoyl, pentanoyl, hexanoyl, and the isomeric forms thereof.

Examples of pharmaceutically acceptable alkali metal ions are lithium, sodium, and potassium.

DESCRIPTION OF THE INVENTION

The compounds of this invention may be prepared by any of several methods known to those skilled in the art. For example, the particular sequence of reactions joining the aromatic rings through the linking alkylene bridge may be selected for synthetic convenience or for maximization of yields. The following Schemes illustrate methods used to prepare the compounds of this invention. Compounds are typically purified by recrystalization from suitable solvents or by chromatography. Unless otherwise specified, the various substituents illustrated in the Schemes are defined as for Formula I, above.

Scheme A illustrates the preferred method used to prepare the compounds of this invention.

SCHEME A

Hydroxypyranones of Formula II react readily with compounds of Formula III (where X represents a halogen, preferably bromine) to form the compounds of this invention, Formula I. A preferred method involves stirring compounds II and III in dimethylformamide in the presence of a base, such as potassium carbonate. By way of illustrating that the particular sequence of reactions may be varied, compounds of Formula I where $R^1$ is an aryloxy function may be prepared by first attaching the alkylene chain to the hydroxypyranone moiety and then by using the method illustrated in Scheme A to attach that adduct to the $R^1$ moiety. Where necessary, substituents $R^2$ may be modified as part of the preparation of starting materials of Formula II. For example, using methods known to those skilled in the art, kojic acid (Formula II, $R^2$ is $CH_2OH$) may be protected and oxidized to the corresponding carboxylic acid and then converted to esters (Formula II, $R^2$ is COOAlkyl). Schemes B and C illustrate several methods for modifying $R^2$ after compounds of Formula I have been prepared.

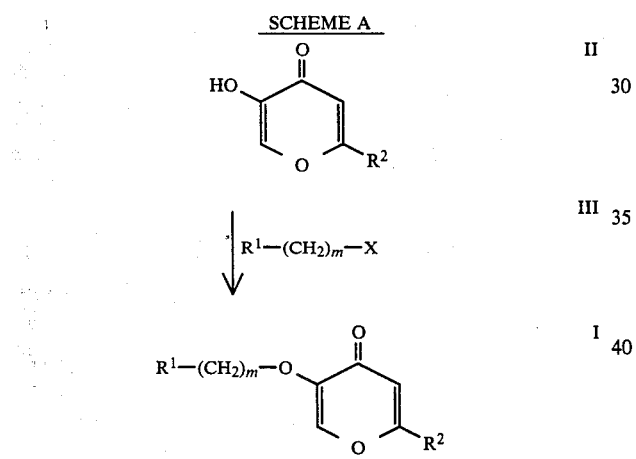

Scheme B Illustrates methods for converting hydroxymethyl compounds of Formula IV (that is, Formula I where $R^2$ is $CH_2OH$) to other compounds of this invention.

SCHEME B

Mild oxidation of alcohols of Formula IV affords corresponding aldehydes, Formula V. A preferred mild oxidation method employs pyridinium chlorochromate in dichloromethane at room temperature. Harsher oxidation conditions convert alcohols of Formula IV to the corresponding carboxylic acids, Formula VI. A preferred oxidation method employs Jones reagent (an adduct of chromic anhydride and aqueous sulfuric acid used in acetone solution). A similar oxidation of aldehydes, Formula V, will also afford carboxylic acids of Formula VI. Esters of Formula VII may then be prepared from the carboxylic acids, V, by the usual methods known to those skilled in the art. For example, a preferred method for preparing methyl esters employs methyl iodide in dimethylformamide in the presence of potassium carbonate, and typically also in the presence of 4 A molecular sieves.

Scheme C illustrates methods used to prepare various other carboxylic acid derivatives of Formula I (that is, where $R^2$ is $COOR^6$) from esters of Formula VII (prepared directly as in Scheme A or indirectly as in Scheme B).

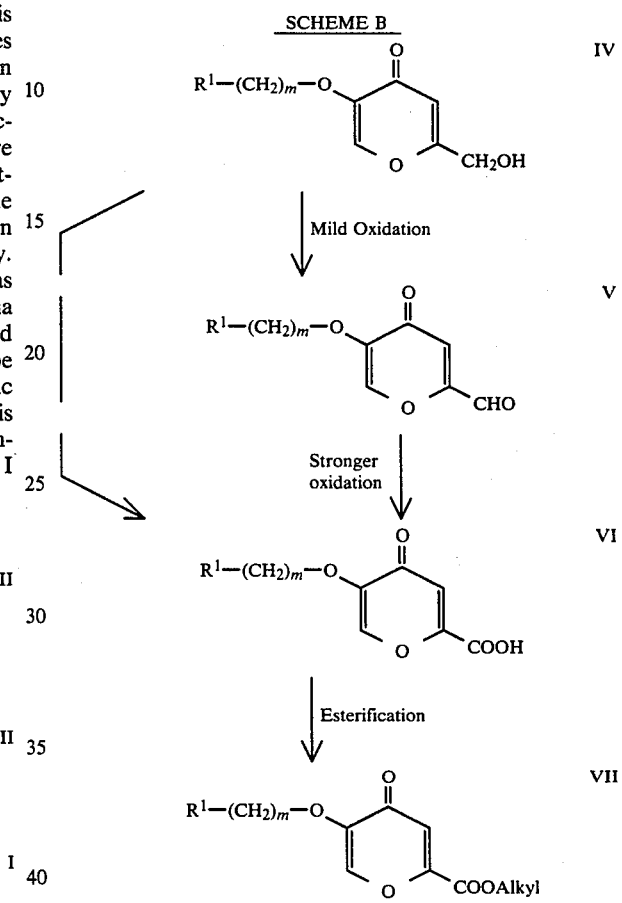

SCHEME C

Saponification of esters, VII, affords metal ion salts of Formula VIII (where $M^+$ is an alkali metal ion). A preferred saponification method employs three-fold sodium hydroxide in 50% (by volume) aqueous ethanol stirred at room temperature. Salts VIII may be converted to the free carboxylic acids, VI, either in situ or after isolation by addition of dilute aqueous mineral acid to solutions of the salts. The carboxylic acids, VI, may be converted to various amine salts (Formula VIII, where $M^+$ represents $R^7R^8R^9R^{10}N^+$) by addition of appropriate organic amines or reconverted to various metal ion salts (Formula VIII, where $M^+$ represents a metal cation) by addition of inorganic bases, such as sodium or potassium hydroxide. Ion exchange affords another method for forming such salts from compounds of Formula VI or VIII.

The compounds of this invention may also be converted to other derivatives. Scheme D illustrates one such conversion.

SCHEME D

Catalytic hydrogenation of compounds of Formula IX, where $R^6$ represents either hydrogen of lower alkyl, affords cyclic ethers of Formula X.

SCHEME C

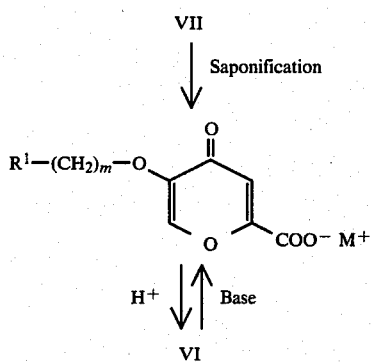

SCHEME D

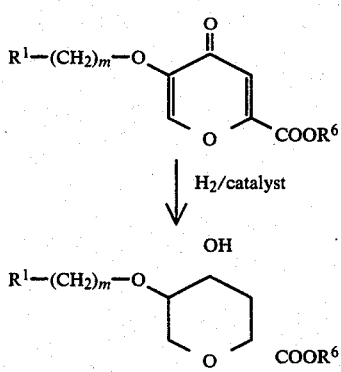

A preferred hydrogenation method employs hydrogen gas at 2 psi pressure and 5% palladium on carbon as catalyst, with an alcohol such as ethanol as solvent. Reduced compounds such as those of Formula X generally retain at least some of the $LTD_4$ inhibitory activity of the parent compounds.

The preferred embodiments of this invention include compounds of the following general structure, Formula XI.

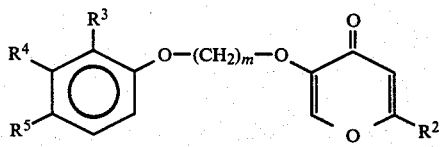

More specifically, the preferred embodiments include compounds of Formula XI wherein $R^2$ is $CH_2OH$, $CH=O$, or $COOR^6$; wherein $R^3$ is lower alkyl (that is, consisting of 1 to 6 carbon atoms, inclusive); wherein $R^4$ and $R^5$ are both hydrogen, or $R^4$ is hydroxy and $R^5$ is acetyl; wherein $R^6$ is hydrogen or lower alkyl; and wherein m is an integer of 1 to 10, inclusive.

The most preferred embodiments of this invention include compounds of the following general structure, Formula XII.

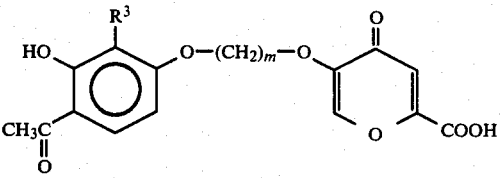

More specifically, the most preferred embodiments include compounds of Formula XII wherein $R^3$ is lower alkyl (that is, consisting of 1 to 6 carbon atoms, inclusive); and wherein m is an integer of 3 to 7, inclusive.

The compounds of this invention exhibited antiallergy activity in guinea pigs, as indicated by antagonism in vitro (isolated ileum segments) of $LTD_4$-induced smooth muscle contractions and by antagonism in vivo of $LTD_4$-induced bronchoconstriction. The antiallergy activity of the compounds of this invention illustrated in the examples was tested by the following methods.

Antagonism of $LTD_4$-induced Smooth Muscle Contractions

Segments of ileum tissue isolated from guinea pigs were mounted in a modified Tyrode solution (8.046 g/l of sodium chloride, 0.200 g/l of potassium chloride, 0.132 g/l of calcium chloride monohydrate, 0.106 g/l of magnesium chloride hexahydrate, 1.00 g/l of sodium bicarbonate, 0.058 g/l of sodium dihydrogen phosphate, and 1.00 g/l of dextrose) containing 0.1 mcg/ml atropine sulfate and 1.0 mcg/ml of pyrilamine maleate and aerated at 37° C. with 95% oxygen and 5% carbon dioxide. The tissue segments were stimulated with two or more concentrations of either $LTD_4$ or bradykinin triacetate (agonists), producing reproducible muscle contractions. The control solution was replaced by a solution or suspension of test compound ($1.0 \times 10^{-5}M$) and incubated for 30 minutes. Each agonist was again introduced to the appropriate solutions and increased doses were added, if necessary, until contractions were approximately equal to those of the previously determined controls or until excessive quantities of agonist were added. For each combination of test compound and agonist, the following dose ratio was calculated: the ratio of agonist concentration in the presence of test compound to the agonist concentration in the absence of test compound that will produce the same contractile response. A concentration of test compound was considered active if it produced a dose ratio against $LTD_4$ significantly ($P<0.05$) greater than a dose ratio obtained in a series of blank treatment tests. (Duplicate tests were conducted for each concentration of test compound, and third tests were conducted if the first two tests were inconsistent.) Compounds that were active against $LTD_4$ but not against bradykinin triacetate were considered selective $LTD_4$ antagonists.

A further measure of receptor affinity, $pA_2$, was also determined for selective $LTD_4$ antagonists. A $pA_2$ value is defined as the negative logarithm of the molar concentration of the antagonist which produces a dose ratio of 2. The $pA_2$ values were calculated by the method of Arunlakshana and Schild, *Br. J. Pharmacol.*, 2, 189 (1947), using Schild plot slopes constrained to $-1$. See R. J. Tallarida and R. B. Murray, *Manual of Pharmacologic Calculations with Computer Programs* (New York: Springer-Verlag, 1981), pp. 33-35.

Antagonism of $LTD_4$-induced Bronchoconstriction

Fasted adult male Hartley guinea pigs weighing 300 to 350 grams were used in this assay. All test animals were pretreated with propranolol and pyrilamine to block the bronchoconstrictive effects of endogenous epinephrine and histamine, respectively, and with indomethacin to block the synthesis of thromboxane $A_2$. The animals were anesthetized with pentobarbital and attached to a rodent respirator. Continuous measurements of intratracheal insufflation pressure were obtained through an intratracheal pressure transducer. After a baseline record was obtained, $LTD_4$ (200 ng) was administered intravenously and agonist-induced changes in intratracheal insufflation pressure were measured. Compounds which antagonize the direct component of $LTD_4$ action on respiratory smooth muscle inhibit intratracheal insufflation pressure increases caused by $LTD_4$. To determine the effect of test compounds on $LTD_4$-induced bronchoconstriction, the compounds were administered to the animals either intravenously (10 mg per kg body weight) or intragastrically (100 mg per kg of body weight) at an appropriate interval prior to the $LTD_4$ challenge. Test compounds were rated active if intratracheal insufflation pressure was significantly ($P<0.05$) reduced relative to vehicle control animals, as assessed by a Student's one-tail t-test.

By virtue of the activity as $LTD_4$ antagonists, the compounds of Formula I are useful in treating asthma and other allergic conditions, inflammation, and coronary vasoconstriction in mammals. A physician or veterinarian of ordinary skill can readily determine whether a subject exhibits the conditions. The preferred utility relates to treatment of asthma. Regardless of the route of administration selected, the compounds of the present invention are formulated into pharmaceutically acceptable dosage forms by conventional methods known to those skilled in the art. The compounds may be formulated using pharmacologically acceptable base addition salts. Moreover, the compounds or their salts may be used in a suitable hydrated form.

The compounds can be administered in such oral dosage forms as tablets, capsules, pills, powders, or granules. They may also be administered intravascularly, intraperitoneally, subcutaneously, or intramuscularly, using forms known to the pharmaceutical art. In general, the preferred form of administration is oral. An effective but non-toxic quantity of the compound is employed in treatment. The dosage regimen for preventing or treating the particular affliction with the compounds of this invention is selected in accordance with a variety of factors, including the type, age, weight, sex, and medical condition of the patient; the severity of the condition; the route of administration; and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention are ordinarily in the range of 0.1 to 10 mg/kg up to about 100 mg/kg orally.

The following examples further illustrate details for the preparation of the compounds of this invention. The invention, which is set forth in the foregoing disclosure, is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted.

PREPARATION OF STARTING MATERIALS AND INTERMEDIATES

Preparation 1
5-benzyloxy-2-(hydroxymethyl)-4H-pyran-4-one

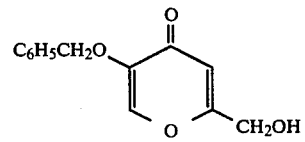

To a stirred solution of 17 g (0.12 mole) of kojic acid and 5.1 g (0.13 mole) of sodium hydroxide in 190 ml of 10:1 (by volume) methanol-water was added dropwise 17.5 g (0.14 mole) of benzyl chloride. After 4.5 hours at reflux, the mixture was allowed to cool and was poured into 200 ml of ice-water. The resultant solid was collected, washed with water, and dried, giving 22.4 g of analytically pure title compound, m.p. 128°–130°.

Analysis. Calcd. for $C_{13}H_{12}O_4$: C, 67.23; H, 5.21. Found: C, 67.24; H, 5.05.

Preparation 2 methyl
5-benzyloxy-4-oxo-4H-pyran-2-carboxylate

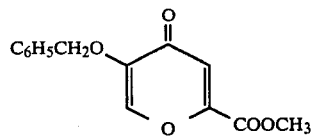

To a solution of 35.5 g (0.15 mole) of 5-benzyloxy-2-(hydroxymethyl)-4H-pyran-4-one (prepared according to Preparation 1) in 2.6 l of acetone was added 143 ml (ca. 0.383 mole) of 2.68M Jones reagent at 0°. The mixture was heated at room temperature for about one hour, then placed on a steam bath for a further ten hours. The reaction was quenched with 250 ml of isopropyl alcohol, insoluble chromium salts were removed by filtration, and the filtrate was concentrated in vacuo to dryness. The crude intermediate was dissolved in aqueous sodium bicarbonate and filtered to remove insolubles. The filtrate was saturated with sodium chloride and acidified (ca. pH 2) with dilute hydrochloric acid, giving 31.0 g of the intermediate carboxylic acid. This intermediate was converted to the title ester without further purification by the following method. A mixture of 28.3 g (ca. 0.12 mole) of the intermediate, 31.8 g (0.23 mole) of anhydrous potassium carbonate, and 21.2 g (0.15 mole) of methyl iodide in 150 ml of dimethylformamide was stirred for ca. 16 hours and then concentrated in vacuo. The residue was dissolved in ethyl acetate, and again filtered. The filtrate was concentrated and the resultant solid was chromatographed on silica gel using ethyl acetate-hexane as eluent. The title compound (25.2 g) was isolated as an analytically pure solid, m.p. 134°–135.5°.

Analysis. Calcd. for $C_{14}H_{12}O_5$: C, 64.61; H, 4.65. Found: C, 64.57; H, 4.59.

Preparation 3 methyl 5-hydroxy-4-oxo-4H-pyran-2-carboxylate

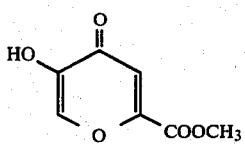

The title product of Preparation 2 (24.0 g, 0.092 mole) was dissolved in a mixture of 360 ml each of tetrahydrofuran and methanol, and then hydrogenated at room temperature using 2 psi of hydrogen and 5% palladium on barium sulfate as catalyst. Insolubles were removed by filtration and the filtrate was concentrated in vacuo to a solid that was recrystallized from acetone, giving 16.6 g (in two crops) of analytically pure title compound, m.p. 183.5°–185.5°.

Analysis. Calcd. for $C_7H_6O_5$: C, 49.42; H, 3.55. Found (first crop): C, 49.31; 3.22. Found (second crop): C, 49.31; 3.31.

Preparation 4 4-(5-bromopentoxy)-2-hydroxy-3-propylacetophenone

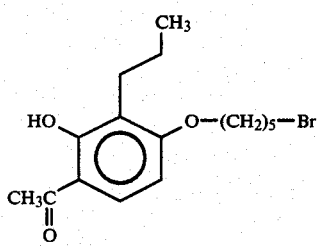

A mixture of 120 g (0.61 mole) of 2,4-dihydroxy-3-propylacetophenone, 284 g (1.23 mole) of 1,5-dibromopentane, and 128 g (0.93 mole) of anhydrous potassium carbonate in 2 l of dimethylformamide was stirred vigorously for six hours at room temperature. Insolubles were removed by filtration and the filtrate was concentrated in vacuo. The oily residue was redissolved in 1 l of 10% ethyl acetate-hexane, refiltered, concentrated to dryness, and purified by high performance chromatography on silica gel. The title compound was obtained as 128 g of an analytically pure colorless oil.

Analysis. Calcd. for $C_{16}H_{23}O_3Br$: C, 55.99; H, 6.75; Br, 23.28. Found: C, 55.72; H, 6.85; Br, 23.51.

Preparation 5 1-(5-bromopentoxy)-2-propylbenzene

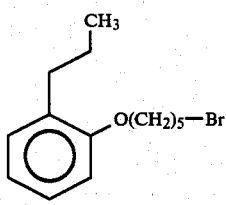

A mixture of 90 g (0.66 mole) of 2-propylphenol, 300 g (1.30 mole) of 1,5-dibromopentane, 120 g of anhydrous potassium carbonate, and 9 g of sodium iodide in 1.2 l of methyl ethyl ketone was stirred at reflux for two days. After cooling, the mixture was filtered to remove insolubles and the filtrate was concentrated in vacuo. The residue was distilled under vacuum to give 120 g of the title compound as an analytically pure oil, b.p. 123°–125° at 0.1 mm Hg.

Analysis. Calcd. for $C_{12}H_{21}OBr$: C, 58.95; H, 7.42; Br, 28.02. Found: C, 58.90; H, 7.43; Br, 27.75.

Preparation 6 2-(3-bromopropoxy)naphthalene

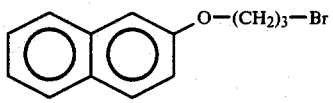

A mixture of 14.5 g (0.1 mole) of 2-naphthol, 30.3 g (0.15 mole) of 1,3-dibromopropane, 15 g of anhydrous potassium carbonate, and 1 g of sodium iodide in 125 ml of methyl ethyl ketone was stirred at reflux for one day. After cooling, the mixture was filtered to remove insolubles and the filtrate was concentrated in vacuo to dryness. The residue was dissolved in dichloromethane, washed twice with 10% aqueous sodium hydroxide, and redried thoroughly in vacuo. The residue was dissolved in hot pentane and filtered hot, and the filtrate was then concentrated under a stream of nitrogen and cooled in a refrigerator, giving the title compound, m.p. 53°–55°.

Analysis. Calcd. for $C_{13}H_{13}OBr$: C, 58.89; H, 4.94; Br, 30.14. Found: C, 59.27; H, 4.91; Br, 29.49.

Preparation 7 2-(2-bromoethyl)naphthalene

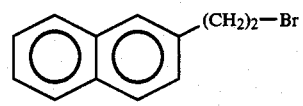

To a solution of 25 g (145 mmole) of 2-(2-naphthyl)ethanol and 67.9 g (259 mmole) of triphenylphosphine in 200 ml of benzene was added in portions 46.1 g (259 mmole) of N-bromosuccinimide. A temperature of 45°–50° was maintained by cooling the reaction mixture as needed in an ice bath. After the mixture was poured into 750 ml of hexane and filtered, the filtrate was diluted with an additional 400 ml of hexane and allowed to stand overnight. The solution was concentrated to dryness and the resultant solid was purified by chromatography on silica gel. The title compound (30.5 g), m.p. 55°–57°, was homogeneous by thin-layer chromatography (5%, 10%, and 15% by volume ethyl acetate-hexane on silica gel plates), and was used in subsequent reactions without further purification.

Preparation 8 2-bromomethyl-1,2,3,4-tetrahydro-2-naphthalene

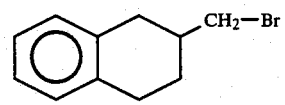

The title compound was prepared by the method of Preparation 7 using 1,2,3,4-tetrahydro-2-naphthalenylmethanol in place of 2-(2-naphthyl)ethanol, except that only slight molar excesses of triphenylphosphine and N-bromosuccinimide were required. After chromatography, the title compound was further purified by distillation at 95° at 0.2 mm Hg pressure, giving 5.5 g of an analytically pure oil.

Analysis. Calcd. for $C_{11}H_{13}Br$: C, 58,69; H, 5.82; Br, 35.49. Found: C, 58.53; H, 6.00; Br, 34.83.

DESCRIPTION OF THE PREFERRED EMBODIMENTS

EXAMPLE 1

5-[5-(4-acetyl-3-hydroxy-2-propylphenoxy)-pentoxy]-2-(hydroxymethyl)-4H-pyran-4-one

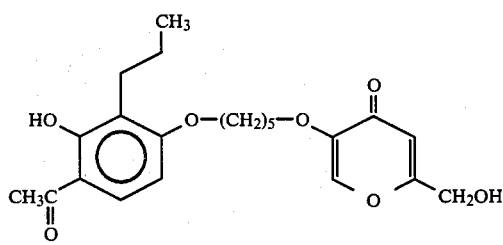

A mixture of 11.4 g (33.2 mmole) of the title product of Preparation 4, 3.78 g (26.6 mmole) of kojic acid, and 8.3 g (60 mmole) of anhydrous potassium carbonate in 150 ml of dimethylformamide was stirred at room temperature for three days. After removing insolubles by filtration, the mixture was concentrated in vacuo and triturated with 300 ml of ethyl acetate. Upon refiltering, the solution was concentrated to dryness, and the residue was dissolved in 50 ml of hot ethyl acetate, filtered, and concentrated. Purification by high performance chromatography on silica gel (using ethyl acetate as eluent) afforded 3.0 g of the title compound, m.p. 94°-95°, as an analytically pure solid.

Analysis. Calcd. for $C_{22}H_{28}O_7$: C, 65.33; H, 6.98. Found: C, 65.19; H, 7.01.

EXAMPLE 2 methyl 5-[5-(4-acetyl-3-hydroxy-2-propylphenoxy)pentoxy]-4-oxo-4H-pyran-2-carboxylate

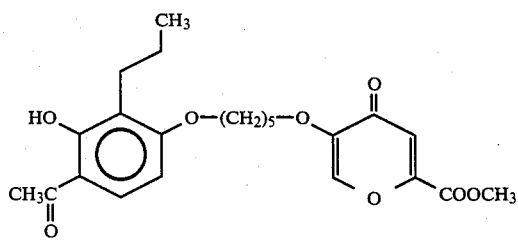

A mixture of 3.43 g (10 mmole) of the title product of Preparation 4, 1.70 g (10 mmole) of the title product of Preparation 3, and 2.76 g (20 mmole) of anhydrous potassium carbonate in 75 ml of dimethylformamide was stirred at 70° for one day. After removing insolubles by filtration, the mixture was concentrated in vacuo to an oily residue, which was dissolved in ethyl acetate, filtered, and reconcentrated. Purification by high performance chromatography on silica gel (using 25% by volume ethyl acetate-dichloromethane as eluent) afforded 2.0 g of the title compound, m.p. 95°-97°, as an analytically pure solid.

Analysis. Calcd. for $C_{23}H_{28}O_8$: C, 63.88; H, 6.53. Found: C, 63.89; H, 6.54.

EXAMPLE 3

5-[5-(4-acetyl-3-hydroxy-2-propylphenoxy)pentoxy]-4-oxo-4H-pyran-2-carboxylic acid

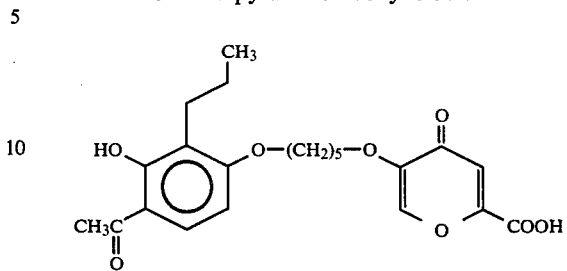

To a solution of 910 mg (2.1 mmole) of the title product of Example 2 in 15 ml of ethanol was added 160 mg (4 mmole) of sodium hydroxide dissolved in 15 ml of water. The mixture was stirred overnight and then acidified (ca. pH 2) with dilute hydrochloric acid. The resulting precipitate was collected by filtration, washed thoroughly with water, and dried under reduced pressure to give 680 mg of analytically pure title compound.

Analysis. Calcd. for $C_{22}H_{26}O_8$: C, 63.00; H, 6.49. Found: C, 62.86; H, 6.43.

EXAMPLE 4

5-[5-(2-propylphenoxy)pentoxy]-2-(hydroxymethyl)-4H-pyran-4-one

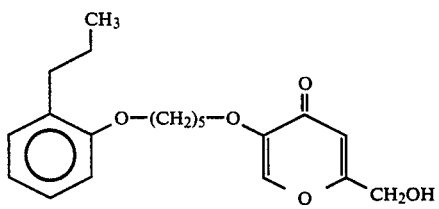

The title compound (4.2 g) was prepared by the method of Example 1, except that the title product of Preparation 5 (7.8 g, 27 mmole) was used instead of the title product of Preparation 4.

Analysis. Calcd. for $C_{20}H_{26}O_5$: C, 69.34; H, 7.56. Found: C, 69.34; H, 7.59.

EXAMPLE 5

4-oxo-5-[5-(2-propylphenoxy)pentoxy]-4H-pyran-2-carboxaldehyde

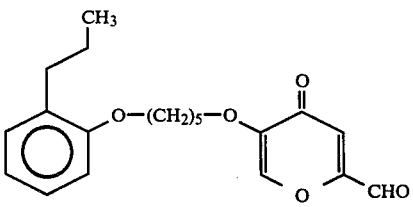

To a stirred solution of 4.44 g (20.6 mmole) of pyridinium chlorochromate in 50 ml of dichloromethane was added 3.46 g (10 mmole) of the title alcohol of Example 4 dissolved in 50 ml of dichloromethane. The resulting slurry was stirred at room temperature for twenty-four hours, then diluted with 100 ml of diethyl ether. The insolubles were removed by decanting and the supernatant was concentrated in vacuo. Purification by column chromatography afforded 1.4 g of the title compound, m.p. 95°–96°.

Analysis. Calcd. for $C_{20}H_{24}O_5$: C, 69.75; H, 7.02. Found: C, 69.52; H, 7.04.

EXAMPLE 6

4-oxo-5-[5-(2-propylphenoxy)pentoxy]-4H-pyran-2-carboxylic acid monohydrate

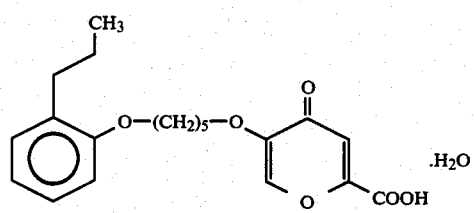

To a stirred solution 3.53 g (10.2 mmole) of the title alcohol of Example 4 in 100 ml of acetone was added dropwise 22.7 ml (ca. 20.4 mmole) of 0.9M Jones reagent. The solution was warmed to 50° and an additional 11.4 ml (10.2 mmoles) of Jones reagent was added. After five hours at room temperature the reaction was quenched with 40 ml of isopropyl alcohol. The insolubles were removed by decanting and the supernatant was concentrated in vacuo. The residue was triturated with ethyl acetate and filtered, and the filtrate was reconcentrated. Recrystallization from ethyl acetate-hexane (2:1 by volume) afforded 1.8 g of the title compound as the monohydrate.

Analysis. Calcd. for $C_{20}H_{24}O_6 \cdot H_2O$: C, 63,49; H, 6.92. Found: C, 63.58; H, 6.52.

EXAMPLE 7 methyl 4-oxo-5-[5-(2-propylphenoxy)pentoxy]-4H-pyran-2-carboxylate

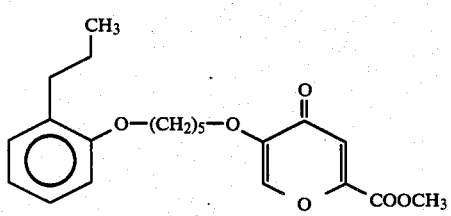

A solution of the title product of Example 7 (1.14 g, 3 mmole) in dimethylformamide was dried overnight by stirring with 4A molecular sieves. Anhydrous potassium carbonate (0.55 g, 4 mmole) and methyl iodide (0.43 g, 3 mmole) were added, and the mixture was stirred at room temperature for thirty-six hours. Insolubles were removed by filtration and the filtrate was concentrated in vacuo to dryness. The residue was purified by column chromatography on silica gel (using 25% by volume ethyl acetate-hexane as eluent), affording 815 mg of analytically pure title compound, m.p. 49°–50°.

Analysis. Calcd. for $C_{21}H_{26}O_6$: C, 67.36; H, 7.02. Found: C, 67.20; H, 7.21.

EXAMPLE 8 methyl 5-[3-(2-naphthalenyloxy)propoxy]-4-oxo-4H-pyran-2-carboxylate

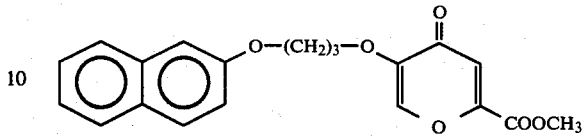

A mixture of 1.70 g (10 mmole) of the title product of Preparation 3, 2.65 g (10 mmole) of the title product of Preparation 6, and 2.76 g (20 mmole) of anhydrous potassium carbonate in 50 ml of dimethylformamide was stirred for three days at room temperature. The title compound, m.p. 90°–91°, was purified and isolated (1.34 g) by the method described in Example 2, except that the chromatographic eluent was 50% by volume ethyl acetate-Skellysolve B.

Analysis. Calcd. for $C_{20}H_{18}O_6$: C, 67.79; H, 5.12. Found: C, 67.56; H, 5.06.

EXAMPLE 9 sodium 5-[3-(2-naphthalenyloxy)propoxy]-4-oxo-4H-pyran-2-carboxylate dihydrate

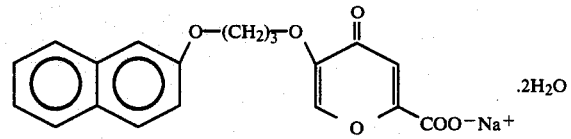

To a solution of 300 mg (0.85) mmole) of the title product of Example 8 in 6 ml of ethanol was added 100 mg (2.5 mmole) of sodium hydroxide dissolved in 6 ml of water. The mixture was stirred overnight and the resultant crystalline solid was collected by filtration. Drying under reduced presure at 80° afforded 116 mg of analytically pure title compound as the dihydrate.

Analysis. Calcd. for $C_{19}H_{15}O_6Na \cdot 2H_2O$: C, 57.29; H. 4.81. Found: C, 57.47; H, 4.25.

EXAMPLE 10 methyl 5-[2-(2-naphthalenyl)ethoxy]-4-oxo-4H-pyran-2-carboxylate

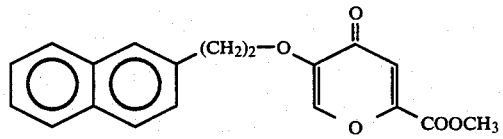

A mixture of 1.70 g (10 mmole) of the title product of Preparation 3, 2.83 g (12 mmole) of the title product of Preparation 7, and 2.76 g (20 mmole) of anhydrous potassium carbonate in 50 ml of dimethylformamide was stirred at 80° for one day. The title compound, m.p. 129°–130°, was purified and isolated (350 mg) by the method described in Example 2, except that (1) the initially isolated crude residue was dissolved by trituration with 50% by volume ethyl acetate-ethanol and (2)

the chromatographic eluent was 40% by volume ethyl acetate-hexane.

Analysis Calcd. for $C_{19}H_{16}O_5$: C, 70.36; H, 4.97. Found: C, 70.74; H, 5.28.

EXAMPLE 11 sodium 5-[2-(2-naphthalenyl)ethoxy]-4-oxo-4H-pyran-2-carboxylate dihydrate

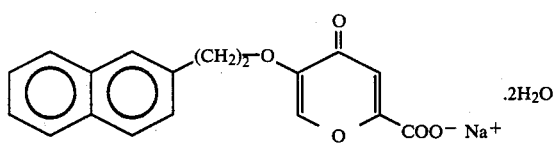

The title compound, isolated as the dihydrate, was prepared by the method of Example 9 using 205 mg (0.63 mmole) of the title product of Example 11 instead of the title product of Example 8.

Analysis. Calcd. for $C_{18}H_{12}O_5Na \cdot 2H_2O$: C, 58.70; H, 4.65. Found: C, 58.99; H, 4.23.

EXAMPLE 12 methyl 5-(1,2,3,4-tetrahydro-2-naphthalenylmethoxy)-4-oxo-4H-pyran-2-carboxylate

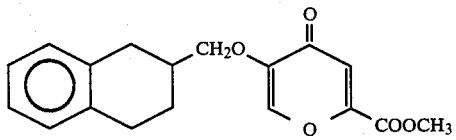

The title compound is prepared by the method described in Example 2 using the title product of Preparation 8 instead of the title product of Preparation 4.

EXAMPLE 13 sodium 5-(1,2,3,4-tetrahydro-2-naphthalenylmethoxy)-4-oxo-4H-pyran-2-carboxylate

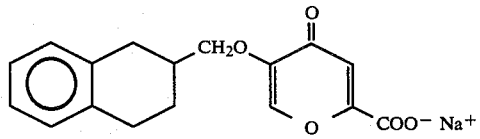

The title compound is prepared by the method of Example 9 using the title product of Example 12 instead of the title product of Example 8.

EXAMPLE 14 methyl 5-[5-(4-acetyl-3-hydroxy-2-propylphenoxy)pentoxy]tetrahydro-4-hydroxy-2H-pyran-2-carboxylate

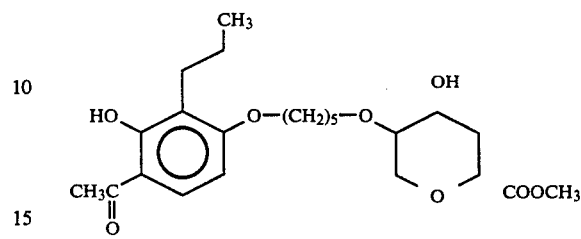

The title product of Example 2 (840 mg, 1.96 mmole) was dissolved in 110 ml ethanol, and then hydrogenated at room temperature using 2 psi of hydrogen and 5% palladium on carbon as catalyst. Insolubles were removed by filtration and the filtrate was concentrated in vacuo, and the incompletely reduced residue (as determined by nmr in $(CD_3)_2SO$) was again hydrogenated. Purification by high performance chromatography on silica gel (using 30% by volume acetone-hexane) afforded 145 mg of the title compound as an oil. Spectral data indicate complete reduction of the pyranone moiety to the hydroxy-substituted cyclic ether.

$^{13}C$ nmr ($CDCl_3$): carbonyl carbon: 203.1 (s) and 171.3 (s) ppm; aromatic ring carbon: 163.2 (s), 162.2 (s), 130.3 (d), 118.3 (s), 114.2 (s), and 102.9 (d) ppm; $CH_2$—O and CH—O carbon: 75.0 (d), 73.2 (d), 69.1 (t), 68.1 (t), 67.3 (d), and 65.0 (t) ppm; methoxy carbon: 52.1 (q) ppm; remaining aliphatic carbon: 33.0, 29.5, 29.0, 26.1, 24.4, 22.8, 22.0, and 14.2 ppm.

proton nmr ($CDCl_3$): δ (ppm) 0.94 (t, 3H, propyl $CH_3$); 1.1–2.6 (m's, 12H, $CH_2$'s); 2.55 (s, 3H, acetyl $CH_3$); 3.3–4.4 (m's, ca. 9H plus $H_2O$, O—$CH_2$'s and O—CH's); 3.78 (s, 3H, methoxy $CH_3$); 6.34 and 7.56 (aromatic CH's).

Infrared: two carbonyl absorptions—1625, 1748 $cm^{-1}$

Analysis. Calcd. for $C_{23}H_{34}O_8$: C, 62.99; H, 7.82. Found: C, 62.15; H, 7.91.

EXAMPLE 15

5-[5-(4-acetyl-3-hydroxy-2-propylphenoxy)pentoxy]tetrahydro-4-hydroxy-2H-pyran-2-carboxylic acid

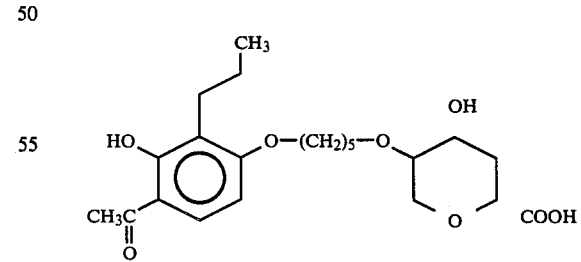

To a solution of 144 mg (0.33 mmole) of the title product of Example 14 in 3 ml of methanol was added 3.3 ml (1.0 mmole) of 0.3M sodium hydroxide. After 90 minutes the solution was concentrated to remove excess methanol and ethyl acetate was added. After the mixture was acidified carefully with dilute hydrochloric acid, the ethyl acetate layer was separated and the aqueous layer washed with additional portions of ethyl acetate. The combined organic layers were dried over sodium sulfate, filtered, and concentrated to dryness. Mass spectrometry indicated a molecular weight of 424, corresponding to the expected title compound.

$^{13}$nmr (CDCl$_3$): nearly identical to that of ester of Example 14, except for loss of methoxy carbon and shift of carboxyl carbon at 171.3 ppm to 174.4 ppm.

What is claimed is:

1. A compound of the formula:

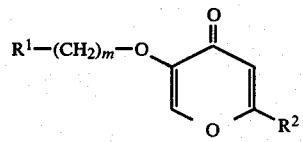

wherein R$^1$ is:

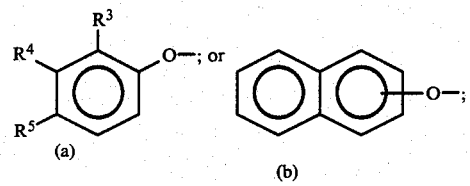

wherein R$^2$ is:
 (a) CH$_2$OH;
 (b) CH=O; or
 (c) COOR$^6$;
wherein R$^3$ is:
 (a) hydrogen;
 (b) alkyl of 1 to 6 carbon atoms, inclusive; or
 (c) alkenyl of 2 to 6 carbon atoms, inclusive;
wherein R$^4$ is:
 (a) hydrogen; or
 (b) hydroxy;
wherein R$^5$ is:
 (a) hydrogen; or
 (b) alkanoyl of 2 to 6 carbon atoms, inclusive;
wherein R$^6$ is:
 (a) hydrogen;
 (b) alkyl of 1 to 6 carbon atoms, inclusive;
 (c) alkali metal ion; or
 (d) R$^7$R$^8$R$^9$R$^{10}$N+;
wherein R$^7$, R$^8$, R$^9$, and R$^{10}$, each being the same or different, are:
 (a) hydrogen; or
 (b) alkyl of 1 to 6 carbon atoms, inclusive;
wherein m is an integer from 1 to 10, inclusive.

2. A compound according to claim 1 having the formula:

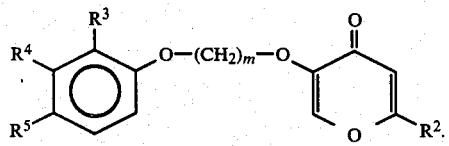

3. A compound according to claim 2 wherein R$^2$ is CH$_2$OH.

4. A compound according to claim 3 having the formula:

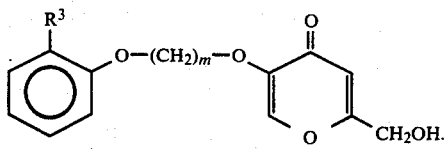

5. A compound according to claim 4, which is 5-[5-(2-propylphenoxy)pentoxy]-2-(hydroxymethyl)-4H-pyran-4-one.

6. A compound according to claim 3 having the formula:

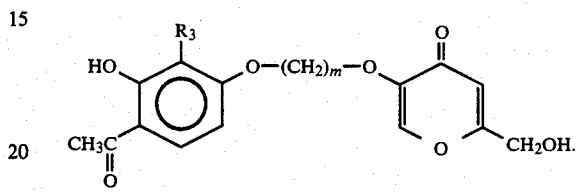

7. A compound according to claim 6, which is 5-[5-(4-acetyl-3-hydroxy-2-propylphenoxy)pentoxy]-2-(hydroxymethyl)-4H-pyran-4-one.

8. A compound according to claim 2 wherein R$^2$ is CHO.

9. A compound according to claim 8, which is 4-oxo-5-[5-(2-propylphenoxy)pentoxy]-4H-pyran-2-carboxaldehyde.

10. A compound according to claim 2 wherein R$^2$ is COOR$^6$.

11. A compound according to claim 10 having the formula:

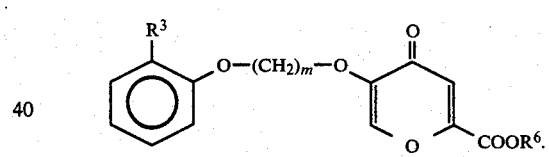

12. A compound according to claim 11, which is 4-oxo-5-[5-(2-propylphenoxy)pentoxy]-4H-pyran-2-carboxylic acid.

13. A compound according to claim 11, which is methyl 4-oxo-5-[5-(2-propylphenoxy)pentoxy]-4H-pyran-2-carboxylate.

14. A compound according to claim 10 having the formula:

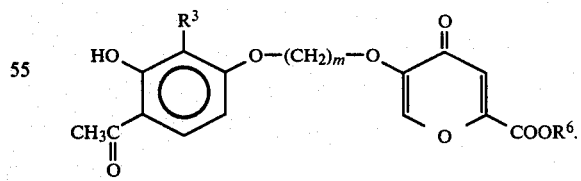

15. A compound according to claim 14, which is 5-[5-(4-acetyl-3-hydroxy-2-propylphenoxy)pentoxy]-4-oxo-4H-pyran-2-carboxylic acid.

16. A compound according to claim 14, which is methyl 5-[5-(4-acetyl-3-hydroxy-2-propylphenoxy)pentoxy]-4-oxo-pyran-2-carboxylate.

17. A compound according to claim 1 having the formula:

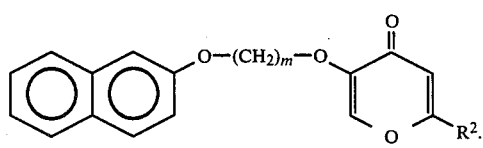
18. A compound according to claim 17 wherein $R^2$ is $COOR^6$.
19. A compound according to claim 18, which is sodium 5-[3-(2-naphthalenyloxy)propoxy]-4-oxo-4H-pyran-2-carboxylate.
20. A compound according to claim 18, which is methyl 5-[5-(2-naphthalenyloxy)propoxy]-4-oxo-4H-pyran-2-carboxylate.
* * * * *

UNITED STATES PATENT AND TRADEMARK OFFICE
CERTIFICATE OF CORRECTION

PATENT NO. : 4,644,071

DATED : February 17, 1987

INVENTOR(S) : Miyano, et al.

It is certified that error appears in the above-identified patent and that said Letters Patent is hereby corrected as shown below:

On the front page of the patent, under the section designating the Inventors, reading "Miyano Masateru" should read -- Masateru Miyano --.

Front page, item [19]: change "Masateru et al." to --Miyano et al.--.

Column 5, the second structure in Scheme D, that portion of the structure reading

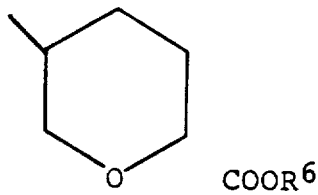

Should read

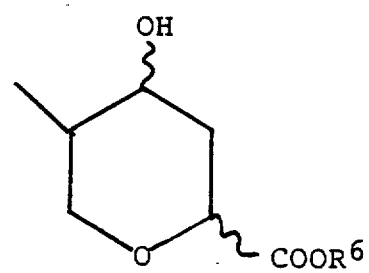

UNITED STATES PATENT AND TRADEMARK OFFICE
CERTIFICATE OF CORRECTION

PATENT NO. : 4,644,071

DATED : February 17, 1987

INVENTOR(S) : Miyano, et al.

It is certified that error appears in the above-identified patent and that said Letters Patent is hereby corrected as shown below:

Column 14, Example 10, line 65, reading "(350 mg)" should read -- (530 mg) --.

Column 16, the first structure, that portion of the structing reading

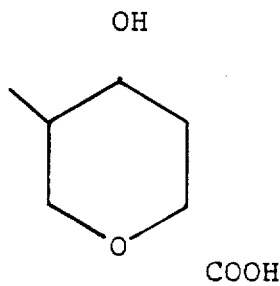

Should read

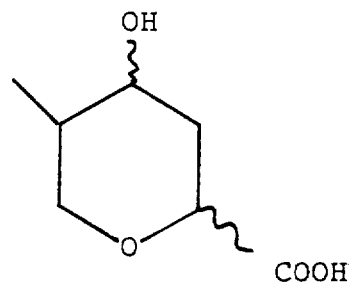

Signed and Sealed this

Fifteenth Day of November, 1988

*Attest:*

DONALD J. QUIGG

*Attesting Officer*  *Commissioner of Patents and Trademarks*